US00PP21433P2

(12) United States Plant Patent
Morishige

(10) Patent No.: US PP21,433 P2
(45) Date of Patent: Nov. 2, 2010

(54) JUNIPER PLANT NAMED 'JAP08'

(50) Latin Name: *Juniperus conferta*
Varietal Denomination: JAP08

(75) Inventor: Takuya Morishige, Chiba (JP)

(73) Assignees: Plant Patent Network, Lake Oswego, OR (US); Fisher Farms, LLC, Gaston, OR (US)

( * ) Notice: Subject to any disclaimer, the term of this patent is extended or adjusted under 35 U.S.C. 154(b) by 8 days.

(21) Appl. No.: 12/322,236

(22) Filed: Jan. 29, 2009

(51) Int. Cl.
*A01H 5/00* (2006.01)

(52) U.S. Cl. ..... Plt./214

(58) Field of Classification Search ..... Plt./214
See application file for complete search history.

*Primary Examiner*—Kent L Bell
(74) *Attorney, Agent, or Firm*—Klarquist Sparkman, LLP

(57) ABSTRACT

A new variety of juniper shrub substantially as herein shown and described, characterized particularly by a combination of creamy-yellow variegated foliage, resistance to heat stress, soft foliage and a relatively slow growth rate.

5 Drawing Sheets

Latin name of genus and species: *Juniperus conferta.*
Variety denomination: 'JAP08'.

OVERALL DESCRIPTION

The present invention relates to a new and distinct variety of Juniper, which has been given the varietal name 'JAP08'. Mr. Takuya Morishige, the inventor, discovered the new plant in Japan as a naturally occurring limb sport mutation of a *conferta* 'Blue Pacific' (unpatented) variety juniper shrub growing in a cultivated area of his nursery in Tokura, Tomisato, Chiba. The new variety differed from the 'Blue Pacific' juniper shrubs growing in this area by its: creamy-yellow variegated foliage, resistance to heat stress, soft foliage and relatively slow growth rate. In this description, the term variegated means a plant with patches of entirely creamy-yellow needles, some needles that are partially creamy-yellow and green, and areas of needles that are entirely green. The quantity of the creamy-yellow color variegations appears to be greater if propagations are made from cuttings exhibiting the creamy-yellow color needles, but variegations still occur in plants propagated from entirely green foliage cuttings.

The original shrub on which the limb sport was discovered had been purchased as a 10 inch liner in the spring season of 2003. Having recognized this limb sport as unique, the inventor observed the limb sport for about 2 years. The original progeny plant was obtained by asexual propagation from the limb sport by softwood cutting. This original propagated plant was grown in smaller containers and eventually was transplanted to a large concrete (25 gallon) container on the nursery property in the spring season of 2008, where it has remained since that time. The originally asexually propagated plant is now about 3 years old from the time of propagation. The originally propagated plant and some subsequent asexually propagated progeny were asexually propagated at the inventor's direction by softwood cuttings at the nursery in Tokura, Tomisato, Chiba, Japan.

As the original limb sport of the new variety and asexually propagated progeny were observed, the uniqueness of this plant became apparent because of its creamy-yellow variegated and green rather than blue-green foliage color, its resistance to heat stress, its soft foliage and its slower growth rate.

These characteristics distinguish the plant from other *conferta* Junipers known to the inventor including 'Blue Pacific' and 'Sun Splash', (unpatented).

The new variety has been asexually propagated by softwood cuttings at the direction of the inventor, in Chiba, Japan. These plants have also been asexually propagated by softwood cuttings in Gaston, Oreg. The asexually propagated progeny exhibit the creamy-yellow variegated and green, rather than blue-green foliage color, its resistance to heat stress, its soft foliage and slow growth rate of the limb sport and of one another, even as smaller plants. This propagation and observation of the resulting progeny have proven the characteristics of my new variety to be firmly fixed and to reproduce true to type. Furthermore, these observations have confirmed that my new variety represents a new and improved variety of juniper plant.

Comparison with 'Blue Pacific' Juniper: 'Blue Pacific' Juniper is a relatively fast growing juniper plant of the blue foliage type that exhibits a horizontal spreading growth habit with very sharp foliage.

Comparison with 'Sun Splash' Juniper: 'Sun Splash' Juniper is believed to be the closest comparable variety. 'Sun Splash' is a relatively fast growing juniper plant having green with golden-yellow variegated foliage, a horizontal spreading growth habit with sharp foliage that tends to brown in direct sunlight from heat stress. The variegations of 'Sun Splash' are more yellow than the creamy-yellow colored variegations of my new variety.

BRIEF DESCRIPTION OF THE DRAWINGS

The accompanying photographs depict the color of the shrub and foliage of my new variety as nearly true as is reasonably possible to make the same in a color illustration of this character.

DETAILED BOTANICAL DESCRIPTION

Figure 1:
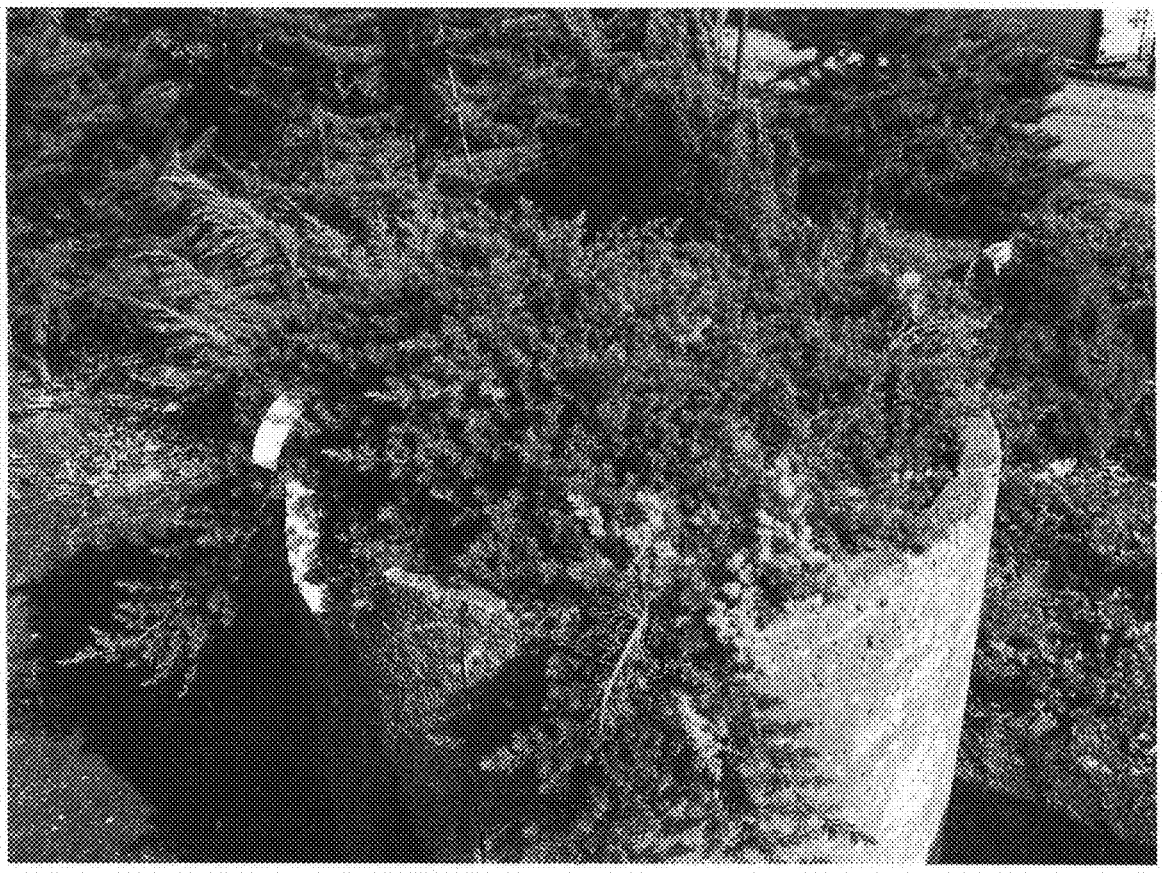
FIG. 1 is a photograph of the original asexually propagated plant of my new variety.
Figure 2:
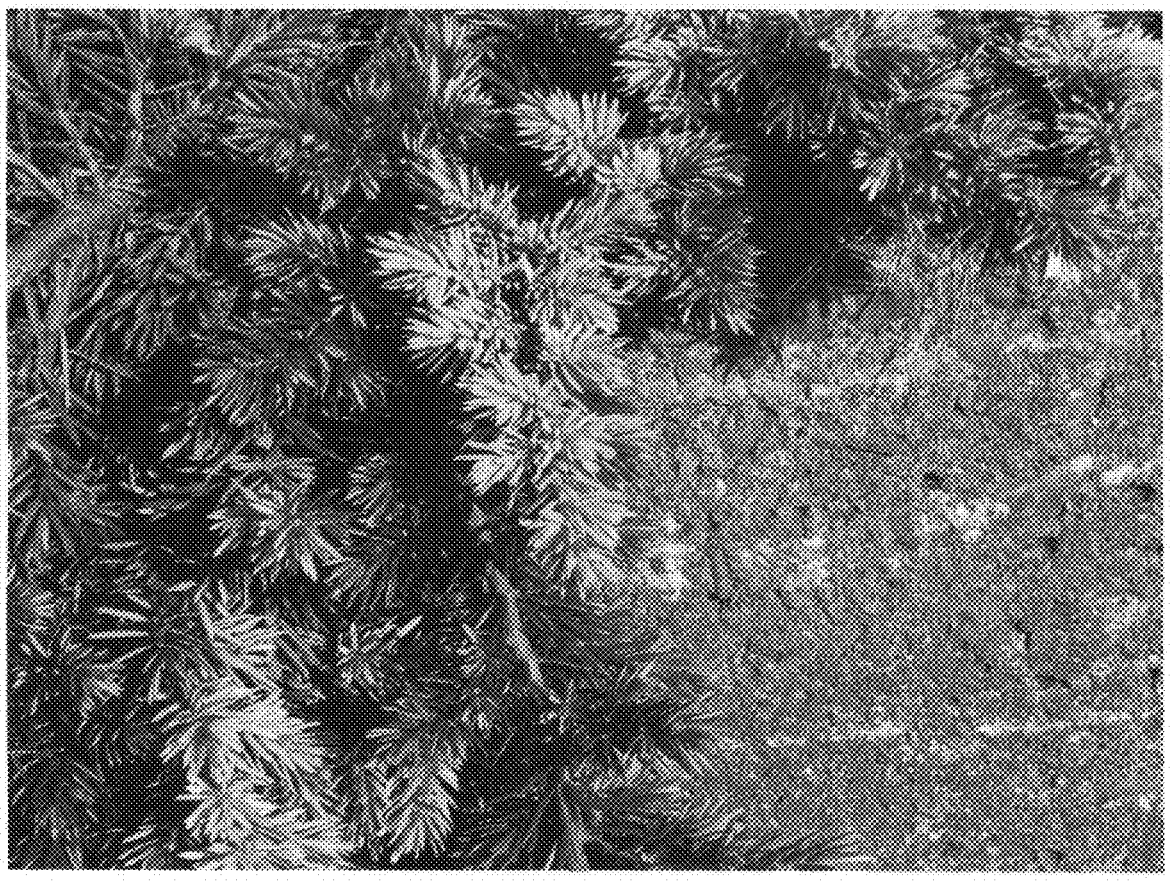
FIG. 2 is a close up photograph of a portion of the plant of FIG. 1.
Figure 3:
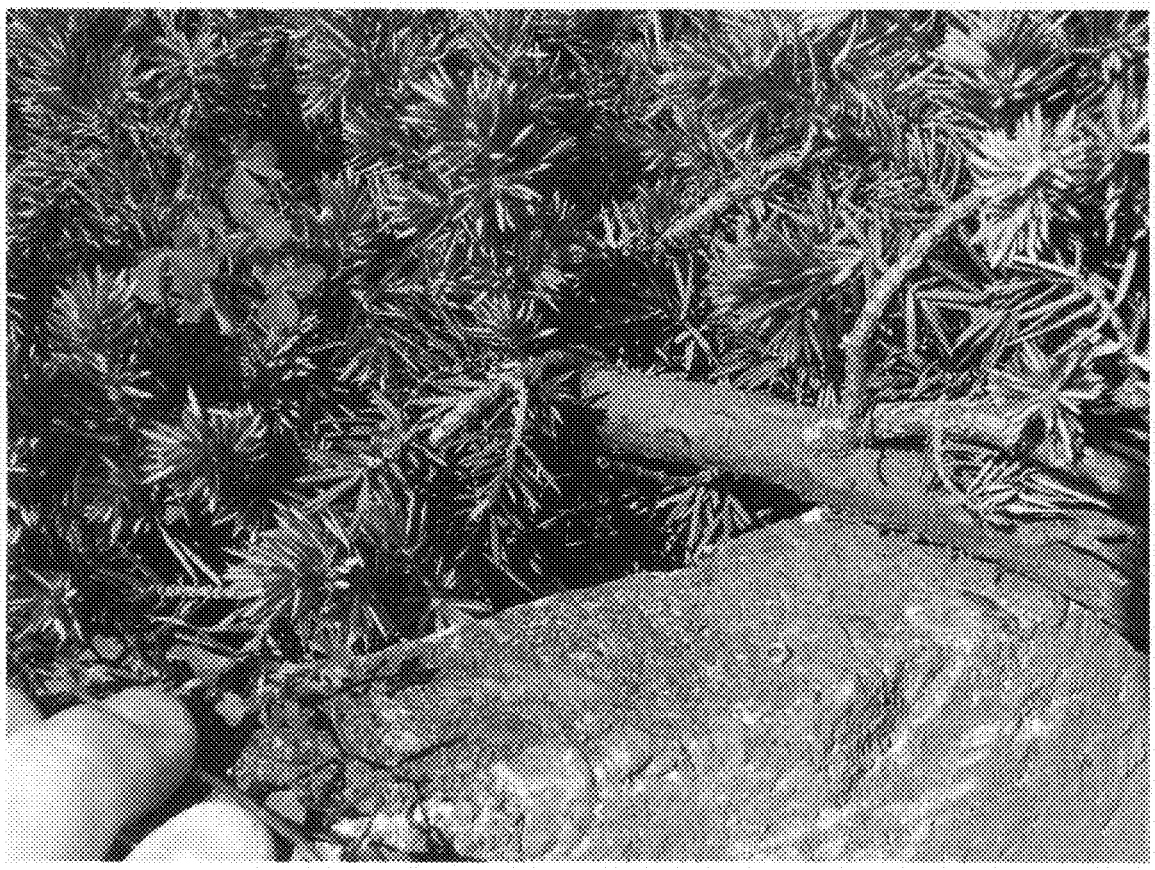
FIG. 3 is a close up photograph showing bark of the plant of my new variety.
Figure 4:
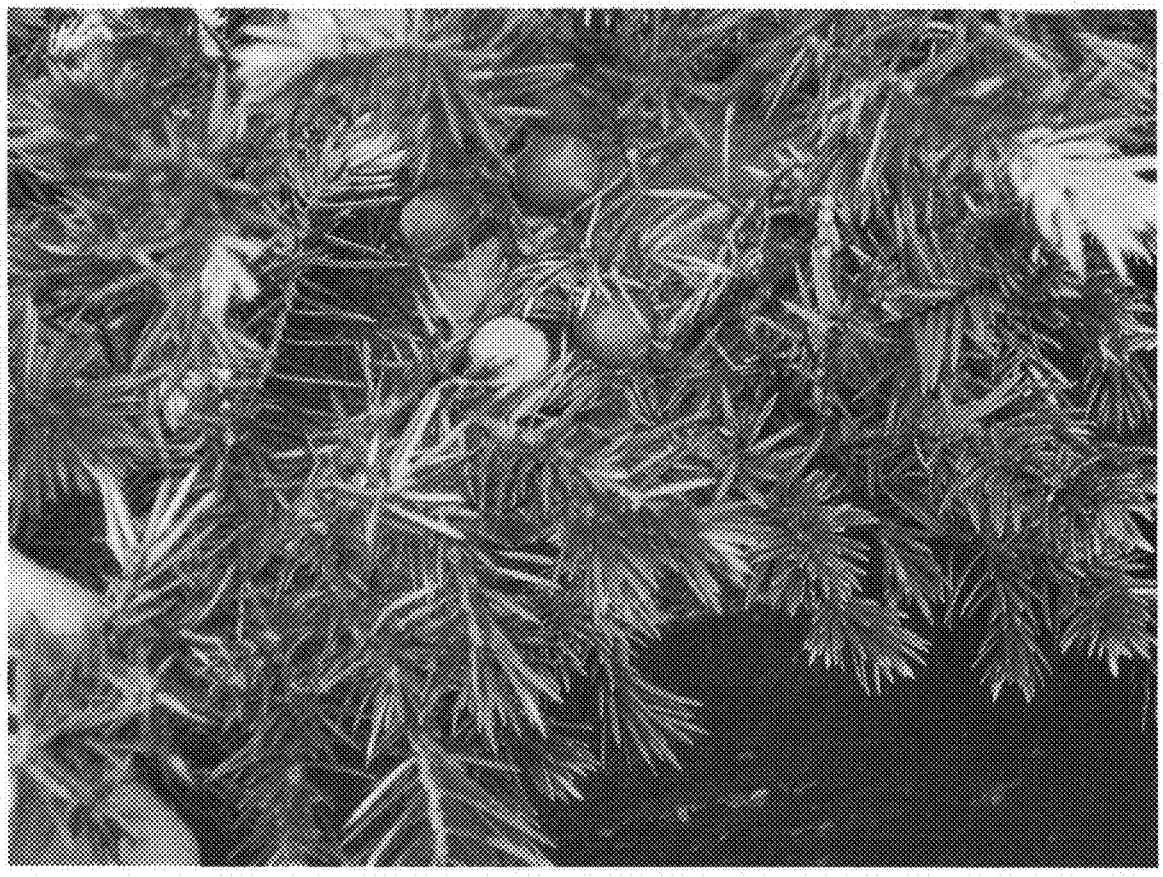
FIG. 4 is a close up photograph showing fruit of the plant of my new variety.
Figure 5:
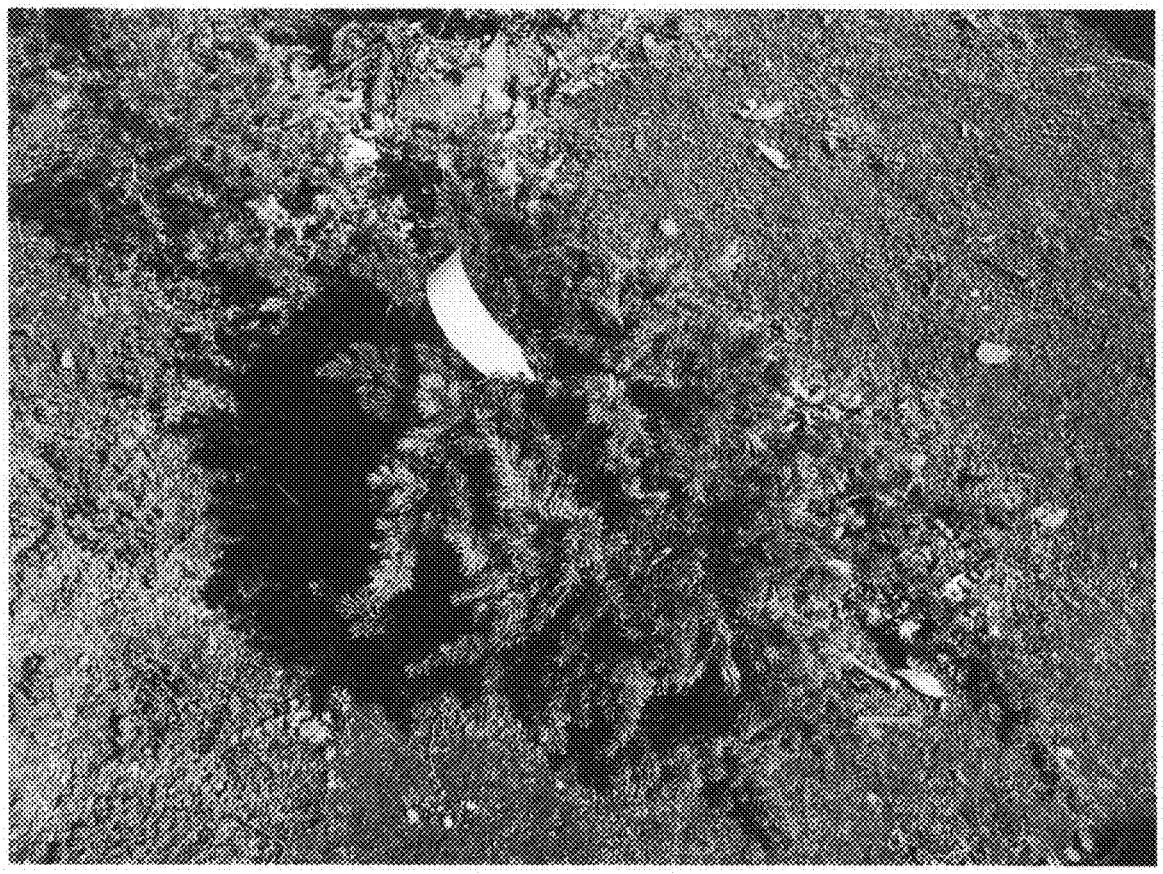
FIG. 5 is a photograph of an asexually propagated plant of my new variety that is about one year old.

Plants of my 'JAP08' variety of *conferta* Juniper shrub are currently growing outdoors at an observation site in Tokura, Tomisato, Chiba, Japan. The site is located in an area of Japan that has a deep, volcanic soil type and receives approximately 52 inches of rain per year. Tokura, Tomisato, Chiba, Japan is in USDA Hardiness Zone 8b. Plants of my new variety are also being grown outdoors at a nursery in Gaston, Oreg. (USDA Hardiness Zone 5).

My new shrub has not been observed under all growing conditions, and thus, variations may occur as a result of different growing conditions. The following is a detailed description of my new variety of shrub with color terminology in accordance with The Royal Horticultural Society (R.H.S.) Colour Chart, copyright 2003, published by The Royal Horticultural Society in London. The observations are of the original asexually propagated plant growing at the nursery in Tokura, Tomisato, Chiba, Japan, and of one year old asexually propagated progeny growing at a nursery in Gaston, Oreg., U.S.A.

Parentage: Discovered as a naturally occurring limb sport mutation of a *Juniperus conferta* 'Blue Pacific' variety shrub growing in a cultivated area of a nursery in Japan.

Shrub shape: Horizontal, spreading canopy, ground cover type plant.

Trunk: The trunk is typical of the species with a spreading growth habit. At about age one year, the originally propagated plant had a diameter of about 0.25 inch in diameter measured four inches above the ground.

Bark: Bark is rough and textured and reddish-grey in color (RHS 166B) with patches of reddish-brown (RHS 180A) on young asexually propagated plants. Mature bark is the same in color.

Truck lenticels: Shape: ovate. Size: 0.10 inch and barely visible to the naked eye. Color: brown (RHS 200B).

Size and growth rate: The originally propagated plant is currently about four inches in height and thirty-six inches in spread, thus providing an overall height to width ratio of about 1:9. The original plant grew in spread (overall width) about eighteen inches since being transplanted to the twenty-five gallon container.

Branching habit: Branching is prostrate and regular. Typical primary branches emerge from the trunk at about a sixty degree angle to the leader. The branching angle does not change with age. The number of lateral branches can vary, in an observation of a group of ten typical three year old branches, the number of lateral branches was 12 per foot. These lateral branches were two years old, with typical lengths of from 4 to 6 inches and typical diameters of about 0.25 inch measured of a distance of 0.5 inch from a joint of the lateral branch to the main branch.

Branches: Surface texture is rough and textured. Color is reddish-grey, the same as the trunk (RHS 166B). Branch lenticels: On a branch having a 0.25 inch caliper, the average lenticel size is 0.10 inches, the same as the trunk. Shape is ovate and barely visibly to the naked eye. Color is brown, the same as on the trunk (RHS 200B).

Foliage: The new plant has leaves that are typical of *J. conferta* in shape, but atypical in that they are soft rather than stiff. Shape: short, needle-like, typically about 0.25 to 0.33 inch long and about 0.08 to 0.15 inch wide with a typical width being 0.10 inch. The fragrance is strong. Summer color of upper leaf surface of green needle: dark green (RHS 135B); summer color of lower leaf surface of green needle: blue-green (RHS 131D). Color of variegations are creamy-yellow (RHS 8D) on both the upper and lower surfaces, with no differences in seasonal color except that the variegation on the lower surface typically tends to fade with age. Slight pubescence, on the underside of the foliage, is blue-green in color (RHS 131D). Overall shape: Base: tapering. Apex: acuminate and somewhat trifolate. Surface texture: smooth. Margin: smooth margin along the entire length of the needle. Petiole: non-existent.

Flowers, fruit and cones: Flowers are non-existent. Fruit is yellow-green (RHS 160B), typically about 0.25 inch to 0.33 inch in diameter, and developing on mature stems in late summer. The fruit shape is rounded, about 0.25 inch in length, the apex is conical with a rounded base, the texture is smooth. Cones are small and tight, typically about 0.33 inch to 0.5 inch in length and about 0.25 inch to 0.33 inch in diameter, reddish-brown in color (RHS 176B), are typical of the species and develop after the fruit appear. The cone shape is conical, the apex is acute, the base is tapering and somewhat rounded and the texture is rough.

Root system: The root system is fibrous and typical of the species.

Pest and disease resistance: Excellent pest and disease resistance to both *Phytophthora* root rot and *Phomopsis* Juniper blight with tolerance to abiotic disorders typical of the species such as heat stress.

Winter hardiness: The plant has been proven hardy in Zone 8b and Zone 5, the two zones in which the plant has been grown.

I claim:

1. A new variety of juniper plant substantially as herein shown and described, characterized particularly by a combination of creamy-yellow variegated foliage, resistance to heat stress, soft foliage and a relatively slow growth rate.

* * * * *